(12) United States Patent
Brown et al.

(10) Patent No.: US 7,803,332 B2
(45) Date of Patent: Sep. 28, 2010

(54) REACTOR TEMPERATURE CONTROL

(75) Inventors: Stephen Harold Brown, Brussels (BE); Paul Hamilton, Chandlers Ford (GB); Keith Holroyd Kuechler, Friendswood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 839 days.

(21) Appl. No.: 11/140,853

(22) Filed: May 31, 2005

(65) Prior Publication Data

US 2006/0270882 A1 Nov. 30, 2006

(51) Int. Cl.
F28D 7/00 (2006.01)

(52) U.S. Cl. .................. 422/201; 422/194; 422/196; 422/234

(58) Field of Classification Search ........... 422/190, 422/191, 198, 194, 201, 234; 585/533, 502
See application file for complete search history.

(56) References Cited

U.S. PATENT DOCUMENTS

| | | | | |
|---|---|---|---|---|
| 2,104,296 | A * | 1/1938 | Frey | 585/314 |
| 2,209,346 | A | 7/1940 | McCausland | |
| 4,141,937 | A | 2/1979 | Bergeron | |
| 4,456,781 | A * | 6/1984 | Marsh et al. | 585/533 |
| 4,511,481 | A | 4/1985 | Shim | 252/32.5 |
| 4,709,111 | A | 11/1987 | Ward | |
| 4,740,645 | A | 4/1988 | Garwood et al. | |
| 4,900,460 | A | 2/1990 | Cardis | 252/46.6 |
| 5,176,840 | A | 1/1993 | Campbell | 252/49.6 |
| 5,205,945 | A | 4/1993 | Cardis et al. | 282/47.5 |
| 5,225,093 | A | 7/1993 | Campbell et al. | 252/51.005 A |
| 5,328,619 | A | 7/1994 | Conary | 252/32.5 |
| 5,358,650 | A | 10/1994 | Srinivasan et al. | 252/45 |
| 5,451,332 | A | 9/1995 | Lawate | 252/32.7 |
| 5,500,140 | A | 3/1996 | Hughes et al. | 252/46.7 |
| 5,538,652 | A | 7/1996 | Farng et al. | 508/231 |
| 5,547,596 | A | 8/1996 | Omiya | 508/188 |
| 5,571,445 | A | 11/1996 | Srinivasan et al. | 508/189 |
| 5,573,696 | A | 11/1996 | Hughes et al. | 508/224 |
| 5,691,283 | A | 11/1997 | Poat et al. | 508/186 |
| 5,693,598 | A | 12/1997 | Abraham et al. | 508/444 |

(Continued)

FOREIGN PATENT DOCUMENTS

DE 820 597 11/1951

(Continued)

OTHER PUBLICATIONS

Nasr, M.R.J. et al., "Application of Heat Transfer Enhancement on Vertical Thermosyphon Reboilers Using Tube Inserts," 16th International Congress of Chemical and Process Engineering, Prauge, Czech Republic, Aug. 22-26 (2004).

(Continued)

*Primary Examiner*—N. Bhat
(74) *Attorney, Agent, or Firm*—Andrew B. Griffis; Leandro Arechederra, III

(57) ABSTRACT

The invention is directed to a reactor system comprising at least one reactor wherein makeup water for said system is preheated by water/steam exiting said reactor. In a preferred embodiment the system comprises plural reactors and the invention provides for each reactor to independently achieve isothermal operating conditions.

9 Claims, 3 Drawing Sheets

U.S. PATENT DOCUMENTS

| | | | |
|---|---|---|---|
| 5,756,429 A | 5/1998 | Ichihashi | 508/192 |
| 6,046,144 A | 4/2000 | Karol et al. | 508/279 |
| 6,048,825 A | 4/2000 | Markson et al. | 508/256 |
| 6,072,093 A | 6/2000 | O'Neill et al. | |
| 6,143,942 A | 11/2000 | Verrelst et al. | |
| 6,171,570 B1 * | 1/2001 | Czuppon | 423/359 |
| 6,180,575 B1 | 1/2001 | Nipe | 508/227 |
| 6,605,572 B2 | 8/2003 | Carrick et al. | 508/198 |
| 6,846,966 B2 | 1/2005 | Lumgair, Jr. et al. | |
| 2002/0147116 A1 | 10/2002 | Carrick et al. | 508/198 |
| 2003/0133858 A1 | 7/2003 | Le | |
| 2003/0176299 A1 | 9/2003 | Guillemet et al. | 508/438 |
| 2004/0266893 A1 | 12/2004 | Filippi et al. | |
| 2005/0061490 A1 | 3/2005 | Filippi et al. | |

FOREIGN PATENT DOCUMENTS

| | | |
|---|---|---|
| EP | 0 186 473 | 12/1984 |
| EP | 0 532 325 | 3/1993 |
| EP | 0 391 653 | 3/1994 |
| EP | 0 531 000 | 2/1997 |
| EP | 0 531 585 | 11/1998 |
| EP | 0 519 760 | 2/1999 |
| EP | 0 450 208 | 12/1999 |
| EP | 1 422 287 | 5/2004 |
| GB | 2 089 674 | 12/1980 |
| JP | 7278142 | 10/1995 |
| JP | 10316987 | 5/1997 |
| JP | 9235581 | 9/1997 |
| WO | WO 94/22990 | 10/1994 |
| WO | WO 00/08119 | 2/2000 |
| WO | WO 01/66677 | 9/2001 |
| WO | WO 02/06930 | 1/2002 |
| WO | WO 03/020858 | 3/2003 |
| WO | WO 03/104620 | 12/2003 |
| WO | WO 2004/067165 | 12/2004 |
| WO | WO 2005/005348 | 1/2005 |
| WO | WO 2005/026640 | 3/2005 |

OTHER PUBLICATIONS

Hengstebeck, R. J., "Petroleum Processing," McGraw-Hill Book Company, Inc. New York, NY, pp. 208-234, (1959).

McElroy Translation of German Patent No. DE 820 597.

* cited by examiner

REACTOR TEMPERATURE CONTROL

FIELD OF THE INVENTION

The invention relates to reactors equipped with circulating fluid such as water and/or steam. In an embodiment, the invention concerns processes for oligomerizing of light olefins in tubular reactors.

BACKGROUND OF THE INVENTION

Many chemical reactions involve the release of significant amounts of heat, which is preferably removed at least partially to avoid impairment of the progress of the desired reaction itself or for other reasons such as product quality or equipment integrity. In the design of many chemical reactors a principal problem is temperature control. This applies in particular to oligomerization reactors, which are often also referred to as polymerization reactors. Some of the large exothermic heat of reaction may be absorbed by heating up the reactants, depending upon the reaction system, but other means are often used to dissipate the rest. To achieve this end, two types of reactors are typically employed with solid catalysts: chamber and tubular, such as generally described in Hengstebeck, "Petroleum Processing", McGraw-Hill (1959), pp. 208-234.

Chamber reactors are typically vertical cylindrical vessels containing several beds of catalysts, with provisions for injecting a cooler quench liquid between them. The use of a chamber reactor for the oligomerization of light olefins to heavier olefins is described, for instance, in U.S. Pat. No. 6,072,093.

Tubular reactors typically are single-pass heat exchangers (e.g., shell-and-tube), with the catalyst normally contained in the tubes. The shell side typically contains a circulating heat exchange fluid. For reasons of more effective heat transfer, it is often preferred to select this fluid such that shell-side conditions can be applied under which the selected fluid at least partly evaporates. A convenient selection is in many instances to use water/steam because inter alia water is readily available, the temperature of the reactor can be controlled by controlling steam pressure, and the system is readily integrated with the water/steam systems typically present in many chemical and petrochemical operations. The use of tubular reactors for the oligomerization of light olefins to heavier olefins is described, for instance, in U.S. Pat. No. 4,709,111.

For any given operation, tubular reactors are typically more expensive to build, take longer to charge and discharge catalyst, and operate with higher concentration of reactants, compared with chamber reactors. Accordingly, it is required that temperature be more closely controlled. This is an area of active research in the industry. See, for instance, U.S. Patent Application Nos. 20030133858, 20040266893, and 20050061490.

Additional references of interest include U.S. Pat. Nos. 4,141,937, 4,456,781, 6,072,093, 6,846,966, WO 200500534, WO 2005026640, and Jafari Nasr and Tahmasebi, "Application of Heat Transfer Enhancement on Vertical Thermosyphon Reboilers Using Tube Inserts", presented at the 16th International Congress of Chemical and Process Engineering, 22-26 Aug. 2004, Prague, Czech Republic Reactor design in a chemical process often is directed to approaching isothermal operation of exothermic reactions. At optimal conditions, vigorous boiling of the liquid, e.g. water, in the shell occurs across the entire surface of the tubes. In a vertical tubular reactor where coolant (e.g. water) enters at the bottom and exits the top, in an inefficient operation the tubes are immersed in a non-boiling liquid phase at the bottom and are contacting primarily or even only vapor (e.g. steam) at the top. Heat transfer efficiency is therefore impaired at top and bottom, and can drop by roughly a factor of 10 relative to optimal conditions. It is extremely difficult to achieve optimal heat transfer conditions with current design practice.

Current reactor design is shown in FIG. 1. The heat exchange fluid is assumed to be water. Water/steam exiting the reactor (not shown) enters via conduit 1 into (or near) the top of a conventional steam drum 10. The water in conduit 1 either drops into the steam drum 10 or is entrained in the steam produced by the heat of reaction and removed along with steam via conduit 2. The steam and entrained water that exits the steam drum 10 via conduit 2 is replaced by make-up water or boiler feed water (BFW) which is fed into the steam drum 10 via conduit 3, typically entering below the water level illustrated by line 11 in FIG. 1. The water entering conduit 3 typically is deaerated by bringing it close to or up to boiling temperature at about atmospheric pressure, and therefore substantially colder than the water already in the drum, where the pressure is typically higher. Water exiting steam drum 10 via conduit 4 is returned to the reactor. As would be recognized by one of ordinary skill in the art, passage through steam drum 10 is induced by at least one of (i) forced flow, such as by mechanically pumping said water/steam, preferably the water in conduit 4, and (ii) thermosyphon circulation.

The present inventors recognized that with this design the temperature difference between the water exiting steam drum 10 and entering the reactor via conduit 4 is substantially different than the temperature of the water exiting the reactor and entering steam drum 10 via conduit 1. Accordingly, isothermal operation is difficult if not impossible to achieve. In such a situation the fluid entering the reactor is subcooled and will not start boiling immediately upon heating. This results in inefficient heat transfer. Approaching isothermal conditions is more readily achieved if the temperature of the water entering the reactor is closer to the temperature of the water exiting the reactor.

One solution has been to preheat the make-up water entering via conduit 3 using an external source of heat. However, such a solution has two problems. First, it is almost always an expensive solution to preheat water in this manner. Second, when only one preheat system and multiple steam drums are in use, it was (heretofore) difficult or impossible to achieve isothermal reactor temperatures in all the reactors simultaneously.

The present inventors have surprisingly discovered an efficient method of maintaining isothermal operation of a reactor by having the water/steam exiting said reactor and the makeup water enter the same phase of the steam drum, i.e., both enter into the liquid phase or both enter into the vapor space above the liquid phase. The inventors have also discovered a method of maintaining isothermal operation of a system comprising multiple reactors.

SUMMARY OF THE INVENTION

The invention is directed to a reactor system comprising at least one reactor and a drum and having a heat exchange fluid circulating through a first conduit from said reactor to said drum and a second conduit from said drum to said reactor, and wherein a portion of said fluid is removed from said reactor system and makeup fluid is added to said reactor system through a makeup fluid conduit connected to said drum, said drum having a liquid phase and a vapor phase above said liquid phase, the improvement comprising connecting said makeup fluid conduit and said first conduit into the same phase of said drum.

In an embodiment the conduit carrying the circulating fluid exiting the reactor is used to preheat the makeup fluid before it enters the drum. In a preferred embodiment, the circulating fluid and the makeup fluid are allowed to mix before they enter the drum. In another preferred embodiment, the reactor system comprises at least one reactor and at least one steam drum, wherein said at least one reactor is connected to said drum by at least one conduit whereby fluid exiting said reactor enters said drum, and at least one conduit whereby fluid exiting said drum enters said reactor, and wherein a makeup fluid conduit is connected to said system (to account for fluid removed from said system), the improvement comprising: (i) connecting the makeup fluid conduit to the conduit containing said fluid exiting said reactor and entering said drum in the vapor phase above the liquid level; (ii) connecting the conduit containing the fluid exiting said reactor to the steam drum below the liquid level (ii.a) through the makeup fluid line or (ii.b) through a conduit separate from the makeup fluid line; or a combination thereof.

In another preferred embodiment the system comprises at least two parallel reactors, each reactor having at least one drum connected thereto by circulating fluid.

In still another preferred embodiment the fluid is water/steam and the water/steam exiting said reactor comprises at least 5 wt % vapor.

In yet another preferred embodiment, the reactor system is a conventional reactor system retrofit so that an operator (or computer control) has an option of adding makeup fluid from the reactor to the steam drum in either the conventional manner, according to the present invention, or a combination thereof.

The invention is also directed to a process comprising carrying out a chemical reaction in system comprising at least one reactor having a drum, said drum having a liquid phase and a vapor phase above said liquid phase, wherein a heat exchange fluid circulates between said reactor and said drum through a first conduit from said reactor to said drum and a second conduit from said drum to said reactor, and wherein a portion of said fluid is removed from said reactor system and makeup fluid is added to said reactor system by a makeup fluid conduit, the improvement comprising adding the fluid from said makeup fluid conduit and the fluid from said first conduit into the same phase of said drum. Preferred embodiments include said process wherein various embodiments of the system according to the present invention (preferred and otherwise) are employed and also said process wherein said chemical reaction is an oligomerization process.

It is an object of the invention to provide a process and a reactor system therefor, operating as close as possible to isothermal conditions and/or wherein the reactor system of the invention automatically maintains the circulating fluid at the optimal temperature.

It is further an object of the invention to more effectively use waste heat to preheat makeup fluid added to a reactor system.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 2:
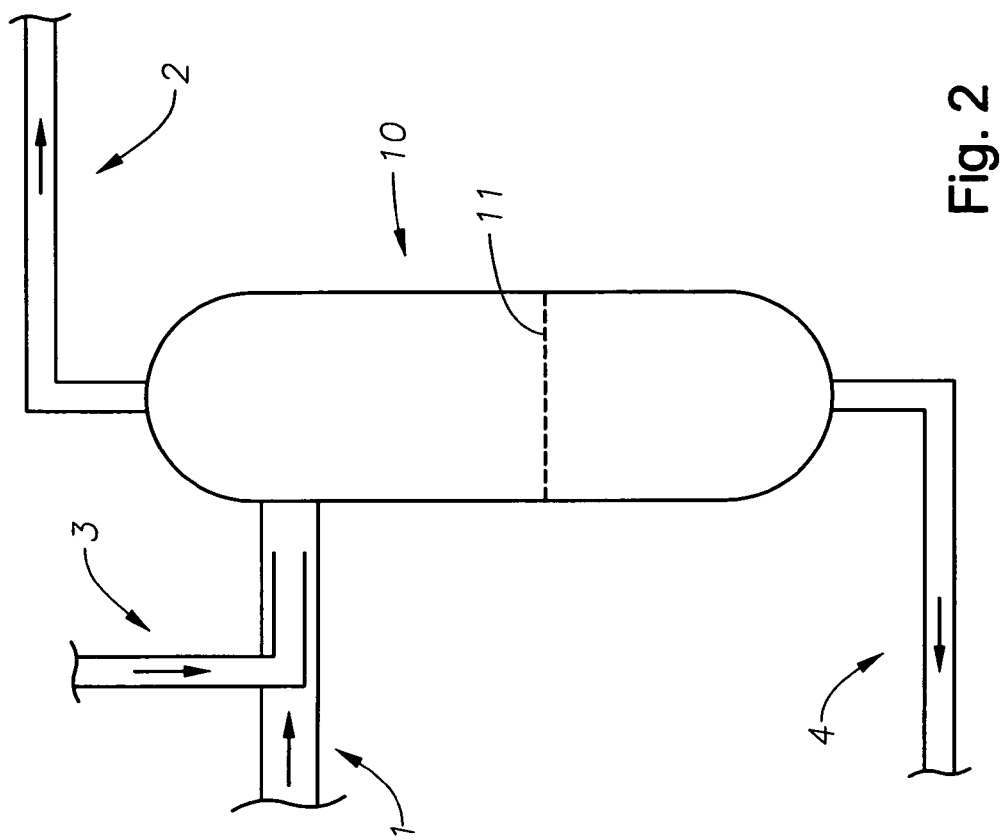
FIGS. 2-4 are partial process flow diagrams illustrating embodiments of the present invention with respect to makeup water and/or water/steam from the reactor to a steam drum.

According to the invention, a reactor system comprising at least one reactor and a drum is provided having circulating fluid, preferably an efficient heat exchange fluid, in a preferred embodiment water/steam, circulating via a first conduit from the reactor to the steam drum and a second conduit from the steam drum to the reactor, wherein a portion of the circulating fluid is removed from the reactor system and makeup fluid is added to the reactor system, the drum having a liquid phase and a vapor phase, the improvement characterized by adding the makeup fluid and the fluid returning to the drum via the first conduit into the same phase of the drum, i.e., either both entering the vapor phase above the liquid level or both entering the liquid phase of the drum.

In an embodiment, the circulating fluid is used as a heat exchange medium, typically as a coolant, however in another embodiment the invention is readily adaptable to systems where the circulating fluid is also the reactor effluent itself, such as the system disclosed in the aforementioned U.S. Pat. No. 4,709,111. More generally the invention is adaptable to any system in which fluid boiling occurs and wherein the fluid that is lost is involved in the temperature control of the system. By way of example, water ordinarily exits as steam from the steam drum, but water is also lost by being purged from the system during "blowdown" to control water quality in the system, including but not limited to total dissolved solids (TDS).

It will be recognized by one of ordinary skill in the art in possession of the present invention that water may be substituted by other fluids such as narrow boiling point hydrocarbons or hydrocarbon mixtures (e.g, narrow cut alkanes). However, for convenience, water will be used as the fluid in the following description. The terms water/steam and steam/water will be used interchangeably.

In an embodiment, the reactor system comprises at least one reactor and at least one steam drum, wherein said at least one reactor is connected by at least one conduit whereby steam/water exiting said reactor enters said steam drum, and at least one conduit whereby water exiting said steam drum enters said reactor, and wherein makeup water is added to said steam drum, the improvement comprising adding the makeup water via the conduit containing said steam/water exiting said reactor and entering said steam drum, so that the makeup water enters the steam drum above the liquid/vapor interface. In one alternative embodiment, the steam/water exiting the reactor may be added to the conventional makeup water line, so that the water/steam it enters the steam drum below the liquid/vapor interface within the steam drum. In yet another alternative embodiment, the conduit containing the steam/water exiting the reactor enters the steam drum below the liquid/vapor interface.

In the case where the makeup water is added to the steam/water conduit line, it is preferably added by a conduit having a smaller diameter than the steam/water conduit exiting the reactor and likewise in the case where the steam/water is added to the makeup water line, it is preferably added via a conduit having a smaller diameter than the makeup water line.

In the case where the makeup water is added to the water/steam conduit, in order to avoid the "steam hammer" effect, the present inventors have found that, in a preferred embodiment, the steam/water exiting said reactor comprise at least 5 wt % vapor. Typically in order to avoid unstable flow the vapor limit is commonly no more than 50 wt % vapor. In other embodiments, the amount of vapor should be no more than 30 wt %. In still other embodiments, the amount of vapor should be no more than 20 wt %. These percentages refer to conditions in the return line, from the reactor to the drum, prior to mixing with BFW water (in cases where the BFW water enters this return line). Fluid in the conduit from the drum to the reactor should be substantially 100% water.

One particular advantage of the present invention is that it allows convenient retrofitting of existing conventional units. Thus, in another preferred embodiment, the reactor system is a conventional reactor system retrofit so that said makeup water and/or water/steam from the reactor enters the steam drum according to the present invention.

The reactor system according to the invention may comprise a conventional reactor such as a reactor in which an exothermic chemical reaction is occurring. The reaction occurring in the reactor may be any reaction, such as a chemical, physical, or nuclear reaction, or it may be simply some mass action effect which produces heat and which needs a circulating fluid to operate. The term "fluid" according to the present invention may be a liquid or vapor or combination thereof, and is preferably water.

The present invention is readily adaptable to exothermic chemical reaction and in preferred embodiments relates to the oligomerization of light olefins to make heavier olefins (e.g., C6 and higher olefins from hydrocarbon streams comprising C2-C5 olefins in a higher olefins reactor comprising a steam boiler coupled with a light olefin oligomerization reactor), but it is also readily adaptable to processes comprising oligomerization of olefin feeds containing one or more C2-C10 olefins, for example C4-C10 internal- or α-olefins, or processes producing one or more C6-C20 oligomerization products or one or more C6-C13 oligomerization products from appropriate feeds, to methanol production (e.g., using a methanol reactor, which is also typically a tubular reactor with steam drums), to mogas production, to distillate production, to cumene production, and to other processes which utilize a circulating heat exchanging fluid.

In one embodiment, the olefin feeds, e.g., light olefins, are obtained by the conversion of an oxygenate, such as methanol, to olefins over a either silicoaluminophosphate (SAPO) catalyst, according to the method of, for example, U.S. Pat. Nos. 4,677,243 and 6,673,978, or an aluminosilicate catalyst, according to the method of, for example, WO04/18089, WO04/16572, EP 0 882 692 and U.S. Pat. No. 4,025,575. Alternatively, the light olefins can be obtained by the catalytic cracking of relatively heavy petroleum fractions, or by the pyrolysis of various hydrocarbon streams, ranging from ethane to naphtha to heavy fuel oils, in admixture with steam, in a well understood process known as "steam cracking".

Preferred processes used for the polymerization of light olefins which may be modified by adopting the reactor system according to the invention include those set forth in U.S. Pat. Nos. 4,855,527, 4,855,528, 5,073,658, 5,108,970, 5,112,519, 5,169,824, 5,234,875, 5,260,501, 5,284,989, 5,672,800, 5,731,486, 5,783,168, 5,866,096, 6,013,851, 6,143,942, 6,300,536, 6,884,916, Canadian Patent No. 2,103,587, WO 01/83407, and WO 93/25476 A1.

By way of non-limiting example and without wishing to be limiting, processes that would benefit from implemenation of the present invention include those oligomerization processes that provide to the polymerization reactor, in addition to the olefin feed, a recycle derived from the reaction product including, for example, one of the materials selected from lower molecular weight oligomers (e.g., separated from higher molecular weight oligomers formed in the reaction product), saturates (such as propane or butane that may have introduced along with the light olefins or formed in the oligomerization reaction) and unreacted olefin feed (e.g., unreacted light olefins that were not converted in the oligomerization reaction and that were separated from the overall effluent exiting the reactor). These may include the oligomerization processes noted above, and also notably those processes that employ a recycle of lower molecular weight oligomers to form additional higher molecular weight olefins, and in particular to the production of distillate products. Distillate products are defined herein as comprising at least two different hydrocarbon carbon number molecules in the range of C8-C36.

In general, distillate product is typified by the boiling ranges and compositions common to conventional petroleum derived hydrocarbon streams such as kerosene, jet fuel and automotive diesel oil, and is fit for such uses. Conveniently, in an embodiment of the present invention, distillate product comprises over 90 wt % C9-C20 hydrocarbons, such as over 95 wt % C9-C20 branched olefins. Exemplary disclosures of such processes include U.S. Pat. Nos. 4,444,988, 4,520,221 and 4,720,600, and WO03/82780.

Distillate may also include linear paraffinic, aromatic and naphthenic species, and all or a portion of the olefinic distillate product obtained from the reaction product may further be saturated with hydrogen, partially or substantially completely, by methods per se well known to the skilled artisan.

By way of further non-limiting example, another process that would benefit from the implementation of the present invention is the manufacture of mogas. As defined herein, mogas comprises at least two different hydrocarbon number molecules in the range of C4-C12. In general, mogas is typified by the boiling range and composition common to conventional petroleum derived motor gasoline fuel used in the function of internal combustion engines. Conveniently, in the present invention, mogas comprises over 80 wt % C5-C11 hydrocarbons, such as over 90 wt % C5-C10 olefins, saturates or aromatics or mixtures thereof. Exemplary disclosures of such processes include U.S. Pat. Nos. 4,444,988 and 4,520,221 (noted above, which co-manufacture mogas along with distillate product), and U.S. Pat. Nos. 3,899,544 and 4,058,576, directed to the conversion of alcohols and ethers to mogas.

It will be recognized by one of skill in the art in possession of the present disclosure that the steam drum device for which a patent is sought may be viewed, in an embodiment as a member of a broad class of devices known as "waste heat boilers" or "steam generators", whose origins predate the refining/petrochemical industry. These devices typically use hot liquids or gasses and water as feedstock and produce lower temperature liquids and gasses and steam as the products. Similar devices have been used to generate high pressure steam for the generation of power or heat. One more recent example is a nuclear power plant, wherein the nuclear core produces a hot heat transfer fluid which is circulated through a heat exchanger to produce steam. The steam goes off to spin a turbine to produce electricity and the cooled heat transfer fluid returns to the nuclear core to be reheated.

Circulation in the reactor may be induced by forced flow, such as by mechanically pumping the fluid through the system or by use of a compressor, or circulation may be thermosyphon (or "thermosiphon") circulation. In preferred embodiments, an object of the invention is to allow the process (tube) side of the one or more waste heat boilers to become more isothermal. This is realized by making the water/steam (shellside) more isothermal. This isothermality is of particular usefulness to waste heat boilers where the exothermic heat of reaction is the source of the "waste heat". Thermosyphon flow is driven by density differences between the heavy liquid in the downleg from the steam drum to the waste heat boiler and the lighter two phase vapor/liquid (steam/water) mixture in the waste heat boiler itself and in the upward leg from the waste heat boiler to the steam drum.

The term "isothermal" as used herein means substantially uniform temperature. One of ordinary skill in the art will appreciate that isothermal conditions can be recognized by, for instance, a stable temperature behavoir, such as a sinusoidal-type temperature behavior varying by, for instance, ±10° C., over at least a portion of the length of the reactor and preferably substantially the entire length of the reactor once steady-state conditions are achieved. The typical length of each reactor in the oligomerization of light olefins to heavier olefins will be about 15 feet (about 4.5 meters) to about 30 feet (about 9 meters), preferably about 20 feet (about 6 meters) to about 30 feet.

In a preferred embodiment, circulation will be induced by thermosyphon effect. In an embodiment wherein the system comprises a steam drum and the reactor is a shell and tube heat exchanger, the steam drum should be located above the reactor to provide the thermosyphon effect required to keep the steam/water mixture circulating. In the preferred embodiment, the water/steam is on the shell side of the waste heat boiler with the source of heat in the tubes. The source of heat will be the exothermic reaction comprising the oligomerization of light olefins, e.g., ethylene, C3, C4, and C5 olefins and mixtures thereof, to heavier olefins, e.g., C6 and higher olefins, preferably C6 to C20 or C6 to C13 olefins. The catalyst packed in the tubes typically will be selected from solid phosphoric acid (sPA), NiO on silica/alumina, $TiO_2$ dispersed on a monolayer of $SiO_2$ on alumina support, one or more zeolites, e.g, ZSM-5, ZSM-22, ZSM-23, ZSM-35, ZSM-57, MCM-22, MCM-23, MCM-41, MCM-49, and MCM-56, which may or may not have metals deposited thereon or therein, and mixtures of these catalysts.

The invention may be readily adapted by one of ordinary skill in the art in possession of the present disclosure to plural reactors, i.e., series or parallel reactors. When multiple reactors are used in parallel, the catalyst for each reactor may be selected independently and in a typical commercial operation each reactor is likely to have a different catalyst; if not a different kind of catalyst, at least a difference in age of the catalyst. This is one of the great advantages provided by the present invention. Since parallel reactors typically will vary in the age and hence activity of the catalyst, the shell side of each reactor in the system of plural reactors likely will be operating under a different pressure. By way of example, a typical system may have one reactor having a relatively new catalyst operating at 10 bar (about 9.9 atm) and another reactor having a relatively old catalyst operating at 40 bar (about 39.6 atm). With conventional multiple reactor/steam drums equipped with a single boiler feed water preheater the operator typically would find an appropriate compromise temperature of the makeup water. However, in a system comprising the apparatus according to the present invention, each individual reactor adjusts the temperature of the makeup water to achieve isothermal conditions specific to that reactor. This is an elegant solution to a difficult problem.

In a preferred embodiment, the source of the makeup water will be split into at least two streams, one entering the steam drum in the conventional manner and one entering, in accordance with an embodiment of the present invention, into the same phase of the steam drum as the water/steam exiting the reactor. Each stream will have a control valve so that the streams may be independently controlled. Typically in a process using such an embodiment wherein circulation at isothermal conditions will be by thermosyphon effect, at startup any necessary makeup water can enter directly into the steam drum in the conventional manner. As isothermal conditions are approached and/or thermosyphon circulation is achieved, the addition of makeup water is preferably solely into the conduit carrying water/steam from the reactor to the steam drum. The control of the valves in such a system can be optimized by one of ordinary skill in the art in possession of the present disclosure by routine experimentation.

FIG. 2 further illustrates an embodiment of the invention. As shown in FIG. 2, similar to FIG. 1, water/steam exiting the reactor (not shown) enters via conduit 1 into (or near) the top of steam drum 10. The water in conduit 1 either drops into the steam drum 10 or is entrained in the steam produced by the heat of reaction and removed along with steam via conduit 2. The steam and entrained water that exits the steam drum 10 via conduit 2 is replaced by make-up water or boiler feed water (BFW) which is fed into the steam drum 10 via conduit 3. According to the invention, the makeup water or BFW in conduit 3 is preheated by the water/steam in conduit 1 prior to entering steam drum 10 into the vapor phase above liquid level 11. Similar to FIG. 1, in FIG. 2 water exiting steam drum 10 is returned to the reactor via conduit 4. No external source of heat is needed to preheat the BFW water (although that remains an optional choice).

It will be appreciated by one of ordinary skill in the art in possession of the present disclosure that FIG. 2 is only one specific embodiment of the invention, and that the invention also relates to any steam drum configuration that mixes hot steam/water returning from the reactor with any portion of the colder water phase in the drum in order to obtain a more uniform temperature throughout the steam drum. The BFW in conduit 3 of FIG. 2 may enter directly into conduit 1 or as shown in FIG. 2 conduit 3 may be of a smaller diameter than conduit 1 and conduit 3 may continue on within conduit 1 for some predetermined distance, preferably ending prior to reaching the steam drum. Typically the BFW will have a distributed release within conduit 1, e.g., it may be sparged into conduit 1 and the combined stream may likewise be sparged into steam drum 10. Preferably good thermal mixing of the BFW with the water/steam exiting from the reactor occurs prior to the combined stream entering the steam drum; substantially optimal configuration of the intermixing of the stream from conduit 1 and conduit 3 can be achieved without more than routine experimentation by one of ordinary skill in the art in possession of the present disclosure.

Figure 3:
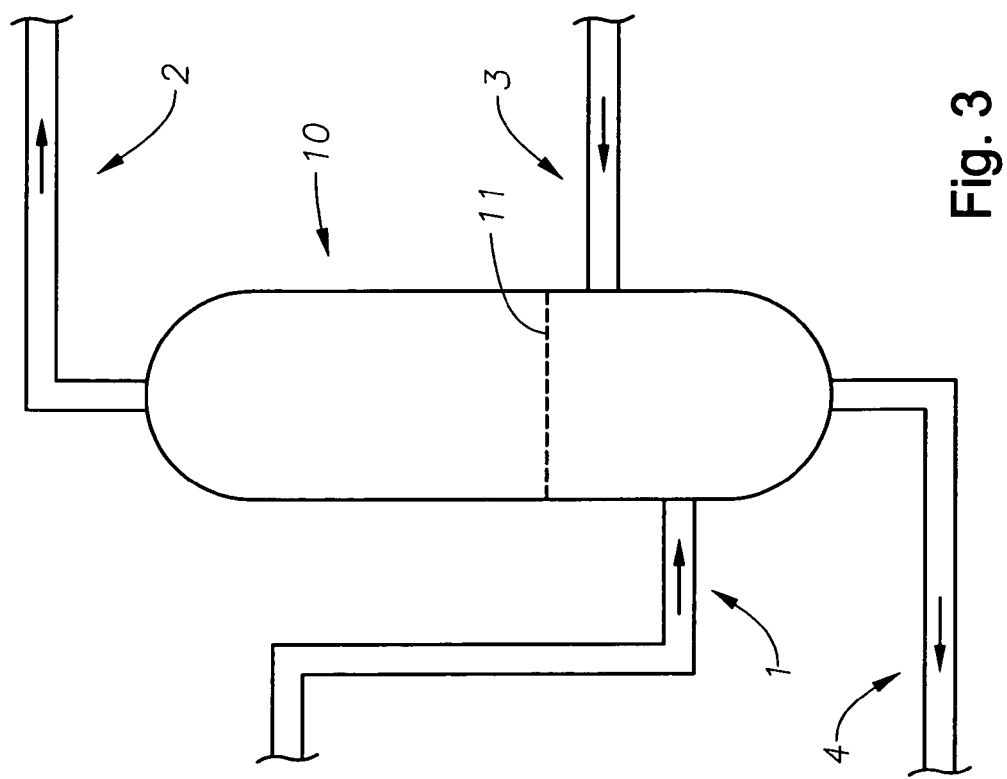

Another embodiment is illustrated in FIG. 3. In FIG. 3, makeup water in conduit 3 enters steam drum 10 in the conventional manner, i.e., below liquid/vapor interface 11, steam exits the system via conduit 2, and water/steam returns to the reactor via conduit 4. The improvement is that the water/steam conduit 1 exiting the reactor now enters the steam drum below the interface 11.

Figure 4:
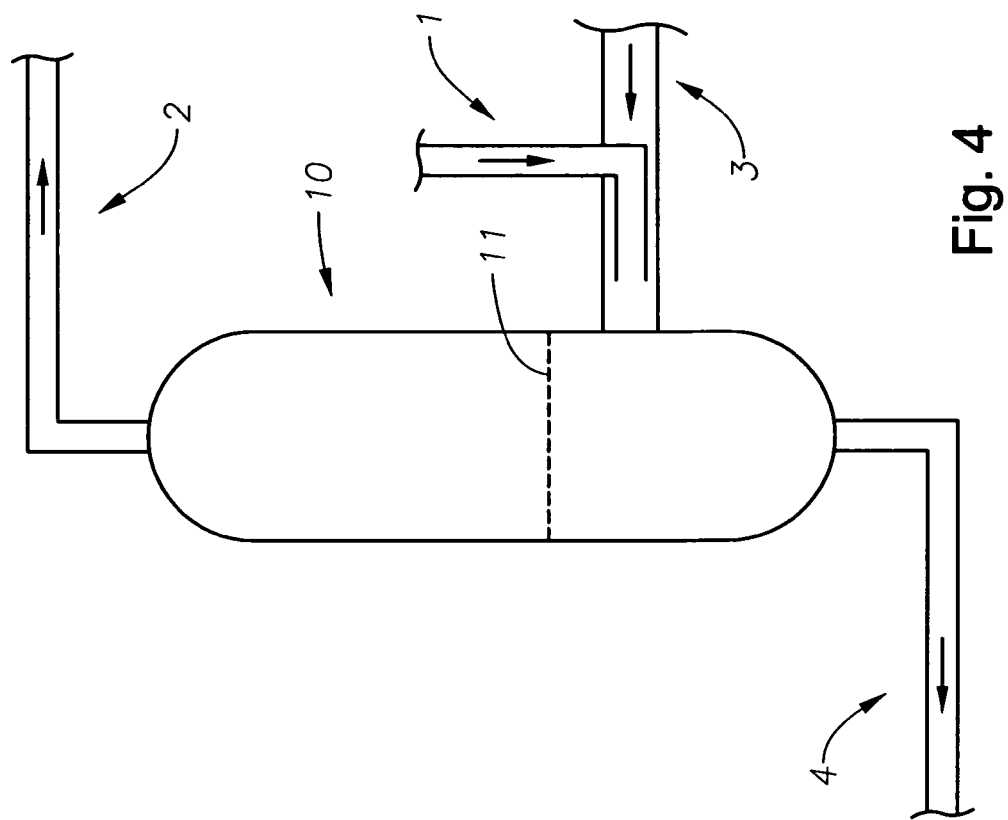

In still another embodiment, as shown in FIG. 4, the water/steam conduit 1 exiting the reactor now enters the makeup water line 3 (below water/vapor interface 11) to preheat the makeup water prior to entering the drum 10. As in the other figures, water returns to the reactor via conduit 4 and steam exits via conduit 2.

Certain appropriate internal steam drum adjustments may be beneficial, whether a conventional steam drum is retrofitted according to the present invention or a new reactor system is built, particularly in the case where the water/steam and makeup water both enter into the liquid phase. For instance, the steam drum may be equipped with one or more distillation trays and a liquid level controller placed in a downcomer (weir). The steam drum may also be mounted higher above the reactor to increase the pressure drop to achieve the proper thermosyphon effect. These sort of engineering details are within the level of skill of the ordinary artisan.

Figure 5:
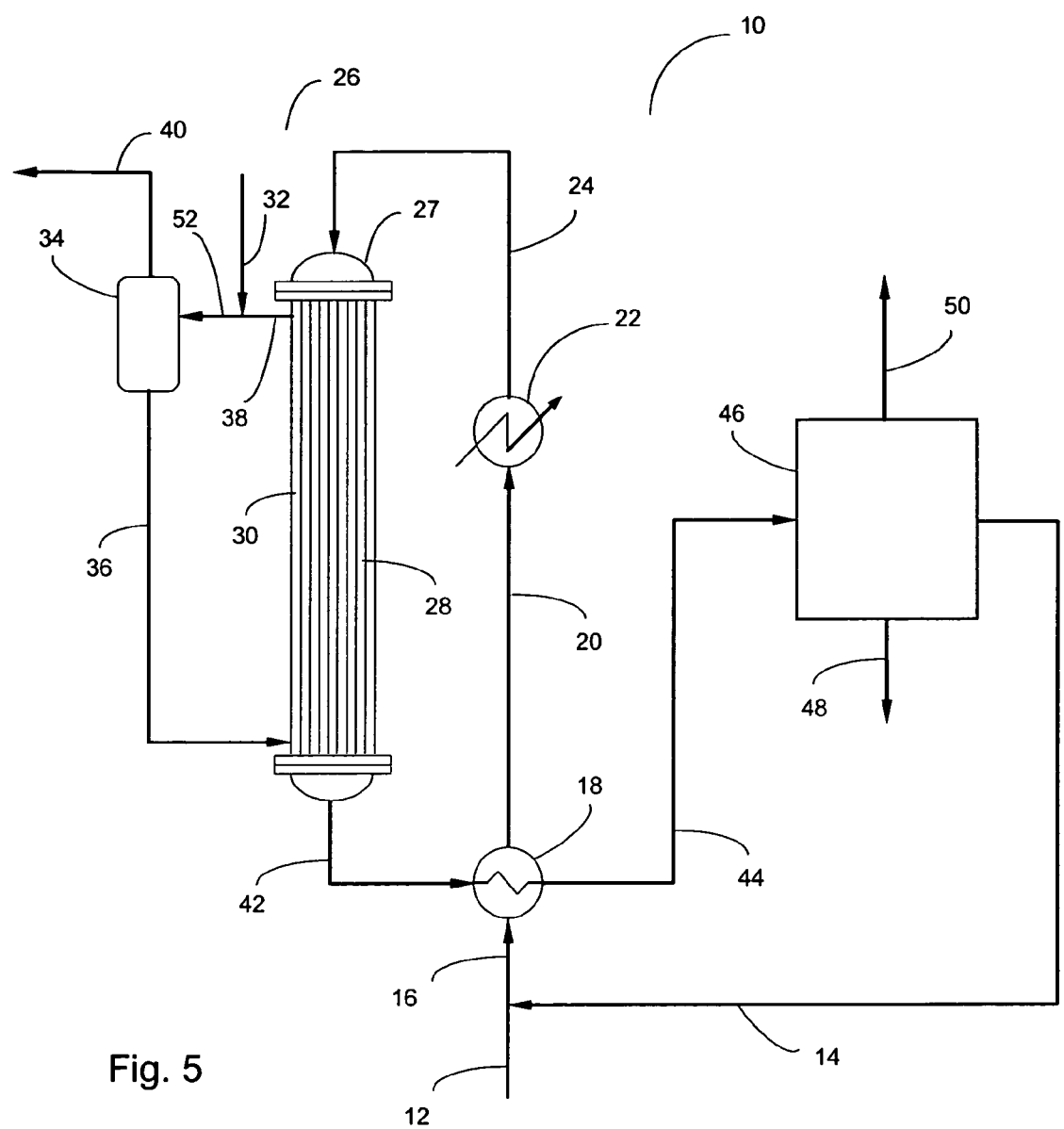
FIG. 5 is a partial process flow diagram comprising an example of applying the method and apparatus of the present invention to an oligomerization process.

Referring now to FIG. 5, there is shown one embodiment of an oligomerization process for producing a hydrocarbon composition according to the invention. The process shown in FIG. 5 employs an olefin oligomerization system 10, comprising a heat exchanger reactor system 26 (comprising elements 34, 27, 22, and 18, discussed below) and a separation device 46 (such as a fractionation tower), among other elements. A fresh feedstock stream, such as one containing at least one $C_3$ to $C_8$ olefin, is provided in line 12, and an olefinic recycle stream (by way of example) containing no greater than 10 wt. % $C_{10}$+olefins is provided in line 14, which in a preferred embodiment are provided such that the mass ratio of the flow of olefinic recycle in line 14 to the flow of feedstock in line 12 is at least 0.5 and no greater than 2.0. The combined materials are provided via line 16 to feed/effluent heat exchanger 18 to form a first heated combined reactor feed in line 20. The first heated combined reactor feed in line 20 is passed through a preheat exchanger 22 to form a second heated combined reactor feed in line 24. The unnumbered line through preheat exchanger 22 represents a heating medium, for example 900 psig (6310 kPa) steam, and the second heated combined reactor feed in line 24 should be at a greater temperature than the first heated combined reactor feed in line 20, but have a temperature no greater than the desired oligomerization reaction temperature in heat exchanger reactor 27.

The second heated combined reactor feed in line 24 is provided to heat exchanger reactor 27, where it flows through plural tubes 28, coming into contact with catalyst contained within the tubes 28. By way of example, the rate of flow of the second heated combined reactor feed in line 24 and amount of catalyst within the tubes 28 of heat exchanger reactor 27 are such that a WRSV of at least 2.3 is achieved, based on the content of olefin in the second heated combined reactor feed in line 24 and the amount of molecular sieve in the catalyst.

The oligomerization reaction thus occurs within tubes 28, generating heat, which passes through the walls of tubes 28 to be absorbed by boiling water flowing around the outside of the tubes in shell side 30 of the reactor 27. The boiling water in shell side 30 is a mixture of steam and liquid water that passes through lines 38 and 52 to disengaging vessel 34. Make-up liquid boiler feed water is provided in line 32, in accordance with the present invention, and combined with the mixture of steam and liquid water coming through line 38 prior to proceeding to disengaging vessel 34 via line 52. The liquid water formed in the disengaging vessel 34 from the steam and liquid water that came through line 52 exit the bottom of disengaging vessel 34 through line 36. The steam generated in the heat exchanger reactor 27 emanates from the top of disengaging vessel 34 through line 40, and may be used, for example, to provide heat in fractionation tower reboilers or to make electricity in turbogenerators. The liquid water in line 36 is then provided to the shell side of heat exchanger reactor 27 to become the boiling water in shell side 30. While not shown in detail in FIG. 5, the conduits represented by lines 32, 38 and 52 would be oriented and configured in the manner described elsewhere herein, for example as shown and described in FIG. 2, ensuring the makeup fluid and the fluid returning to the drum via the first conduit enter into the same phase of the drum, i.e., either both entering the vapor phase above the liquid level or both entering the liquid phase of the drum.

The presence of a relatively pure heat exchange component, such as water, in a boiling state on the shell side 30 provides an almost constant temperature within shell side 30 and can, given other appropriate design considerations of heat exchanger reactor 27, provide for a very close approach to isothermal conditions for the reaction occurring within the tubes 28. The difference between the highest and lowest temperature within and between all tubes 28 in heat exchanger reactor 27 is preferably no greater than 40° F. (22° C.), conveniently no greater than 30° F. (17° C.), or even no greater than 18° F. (10° C.). Further, this configuration of heat exchanger reactor system 26 allows for good control of the reaction temperature within tubes 28 through controlling the pressure within the disengaging vessel 34 (sometimes called a "steam drum"). The pressure in the steam drum 34 controls the temperature at which the water will boil in shell side 30 one of the key factors governing the rate of absorption of the heat of reaction within tubes 28.

As the catalyst in tubes 28 deactivates with time on stream, a given level of conversion of olefins can be obtained by increasing the pressure in steam drum 34, thus increasing the boiling temperature of the fluid in shell side 30, and increasing the temperature of the oligomerization reaction within tubes 28. Of course, the temperature of the boiling fluid in shell side 30 must be kept lower than the desired oligomerization reaction temperature within tubes 28, conveniently at least 5° C. lower, such as at least 10° C. lower, including at least 15° C. lower and even at least 20° C. lower, but typically not exceeding 40° C. lower to reduce the risk of introducing too great a radial temperature gradient within tubes 28 and decreasing the isothernality of the oligomerization reaction within tubes 28.

One design consideration for approaching isothermal conditions in heat exchanger reactor 27 is a relatively small diameter for the tubes 28, for example, an outside diameter of less than about 3 inches (7.6 cm), conveniently less than about 2 inches (5.1 cm), such as less than about 1.5 inches (3.8 cm), and an inside diameter commensurate with the desired pressure rating for the inside of the tubes 28. This provides a relatively small resistance to heat transfer relative to the heat generated per unit volume of reaction space within tubes 28. Another such design consideration is a relatively long length for tubes 28, such as greater than about 5 meters, including greater than about 7 meters, conveniently greater than about 9 meters, which reduces the heat release per unit volume of reaction within tubes 28 and also promotes isothermality.

The oligomerization reaction product exits heat exchanger reactor 27 through line 42, and is provided to feed/effluent exchanger 18. The cooled reaction product exits feed/effluent exchanger 18 through line 44, and is provided to separation device 46. Separation device 46 may include one or more well known elements, such as fractionation columns, membranes, and flash drums, among other elements, and serves to separate the various components in the cooled reaction product in line 44 into various streams having differing concentrations of components than the cooled reaction product in line 44, including, by way of example, a manufactured distillate product in line 48 and an olefinic recycle stream containing, in a preferred embodiment, no greater than 10 wt. % C10 olefins in line 14. Additionally, one or more purge streams may be produced by separation device 46 and exit via line 50. Such purge streams in line 50 conveniently include streams richer in saturated hydrocarbons than the feedstock stream in line 12, such as a $C_4-$ rich stream containing unreacted butylenes and relatively concentrated $C_4-$ saturates, or a portion of material of identical or similar composition to that of the olefinic recycle in line 14 and relatively concentrated in $C_5+$ saturates. Providing such purge streams is convenient in controlling the partial pressure of olefins provided for reaction in heat exchanger reactor 27.

EXPERIMENTAL

The following examples are meant to illustrate the present invention. Numerous modifications and variations are possible and it is to be understood that within the scope of the appended claims, the invention may be practiced otherwise than as specifically described herein.

Example 1

Figure 1:
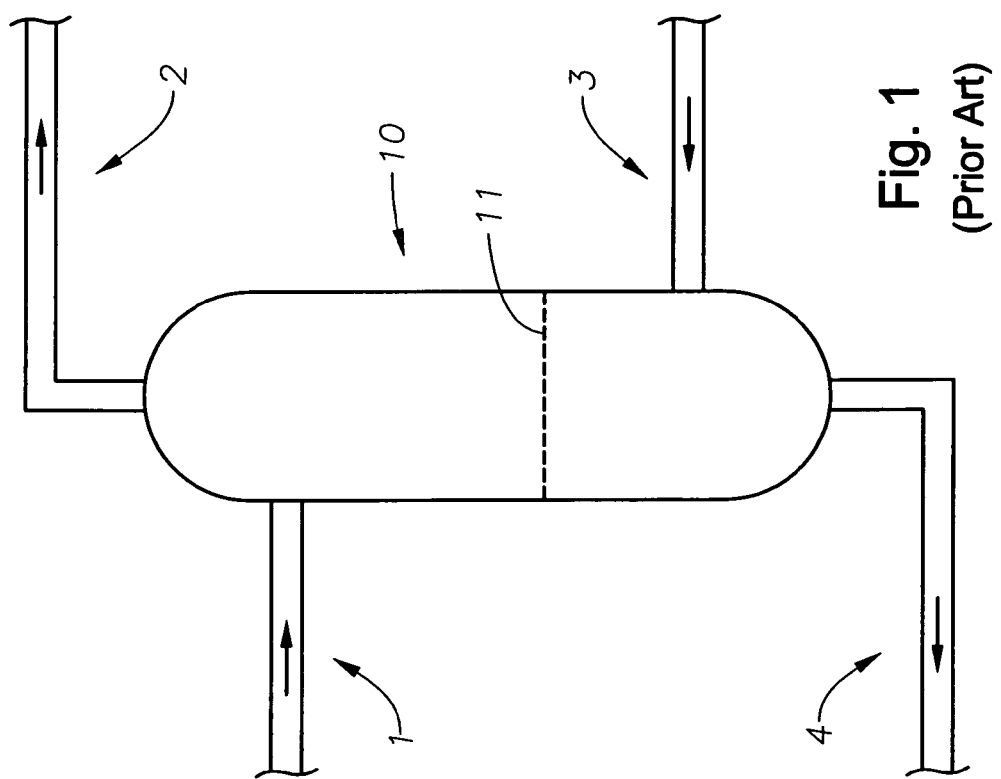
FIG. 1 is a partial process flow diagram illustrating the prior art with respect to makeup water addition to a steam drum.

The following measurements were made for a commercially-operating unit for the oligomerization of light olefins in a conventional tubular reactor having the design, with respect to the steam drum, illustrated in FIG. 1. The operating outlet steam temperature on the shell side of the reactor was 240.0° C. The water going from the steam drum to the shell side of the reactor (inlet) was cooled by mixing with the makeup water down to 234.8° C. Accordingly, the water from the steam drum to the reactor shell-side inlet (conduit 4 in FIG. 1), during steady state conditions, was seeing a temperature 5.2° C. lower than the reactor shell-side outlet steam/water (conduit 1 in FIG. 1).

Example 2

The following measurements were made for an operating unit for the same reaction and in a tubular reactor system nearly identical to that in Example 1 except retrofitted according to the present invention and having the design, with respect to the steam drum, illustrated in FIG. 2. The operating outlet steam temperature on the shell side of the reactor was 240.4° C. (an operating point chosen as close as possible to the one selected in Example 1). The water going from the steam drum to the shell side of the reactor (inlet) was now 238.6° C. Accordingly, the water from the steam drum to the reactor shell-side inlet (conduit 4 in FIG. 2), during steady state conditions, was seeing a temperature 1.8° C. lower than the reactor shell-side outlet steam/water (conduit 1 in FIG. 2). Clearly this is a much closer approach to isothermal operation than achieved with the conventional apparatus.

While it is always difficult to make a comparison of catalytic systems because of the tremendous number of variables involved (age of catalyst, packing density, and so forth), the above comparison was made using substantially similar conditions, except as noted in the description above, within routine experimental variance. The comparison fairly illustrates that, whereas for a typical conventional reactor system carrying out a typical oligomerization process, isothermal conditions are approached much more close in a system operating according to the present invention when compared with a conventional system.

While the illustrative embodiments of the invention have been described with particularity, it will be understood that various other modifications will be apparent to, and can be readily made by, those of ordinary skill in the art without departing from the spirit and scope of the invention. As an example, the embodiments, preferred and otherwise, may be combined in numerous ways that will be apparent to one of ordinary skill in the art. Accordingly, it is not intended that the scope of the claims appended hereto be limited to the embodiments and other descriptions set forth herein but rather that the claims be construed as encompassing all the features of patentable novelty which reside in the present invention, including all features which would be treated as equivalents thereof by those skilled in the art to which the invention pertains. Certain embodiments, nevertheless, are particularly preferred, including a reactor system comprising at least one reactor and a drum and having a heat exchange fluid circulating via a first conduit from said reactor to said drum and a second conduit from said drum to said reactor, and wherein a portion of said fluid is lost from said reactor system and makeup fluid is added to said reactor system via a makeup fluid conduit, said drum having a liquid phase and a vapor phase above said liquid phase, the improvement comprising adding said makeup fluid conduit and said first conduit into the same phase of said drum; and also preferred embodiments selected from one or more of the following, which may be combined as would be recognized as appropriate by one of ordinary skill in the art in possession of the present disclosure: wherein said makeup fluid conduit and said first conduit enter into the liquid phase of said drum; wherein said makeup fluid conduit and said first conduit enter into the vapor phase of said drum; wherein the improvement further comprising: (i) adding said makeup fluid conduit into said first conduit, said first conduit entering said drum into said vapor phase; (ii) adding said first conduit into said makeup fluid conduit, said makeup fluid conduit entering said drum in said liquid phase; (iii) adding said first conduit and said makeup fluid conduit separately into said steam drum below the liquid level. Also, a reactor system comprising at least one reactor and a drum and having a heat exchange fluid circulating via a first conduit from said reactor to said drum and a second conduit from said drum to said reactor, and wherein a portion of said fluid is lost from said reactor system and makeup fluid is added to said reactor system, the improvement comprising adding said makeup fluid to said first conduit; and also preferred embodiments selected from one or more of the following, which may be combined as would be recognized as appropriate by one of ordinary skill in the art in possession of the present disclosure: wherein said reactor is a polymerization reactor; wherein said reactor is an oligomerization reactor; wherein said reactor is a tubular reactor; wherein said reactor is a tubular polymerization reactor; wherein said reactor is a shell-and-tube polymerization reactor comprising at least one tube having a polymerization catalyst therein, especially wherein said catalyst is selected from the group consisting of solid phosphoric acid (SPA), zeolites, and mixtures thereof; wherein said drum is a steam drum having steam discharge outlet, an inlet to receive water/steam from said reactor, and an outlet comprising a conduit to said reactor, particularly wherein said drum further comprises an inlet to receive makeup water; wherein said fluid is selected from water, steam, and a mixture thereof; wherein said fluid in said first conduit consists essentially of from about 5 wt % to about 50 wt % steam and about 95 wt % to about 50 wt % water, or wherein said fluid in said first conduit consists essentially of from about 5 wt % to about 30 wt % steam and about 95 wt % to about 70 wt % water, or wherein said fluid in said first conduit consists essentially of from about 5 wt % to 20 wt % steam and about 95 wt % to 80 wt % water; wherein said system comprises at least two reactors, each reactor having a steam drum fluidly connected thereto. Also a process comprising carrying out a chemical reaction in system comprising at least one reactor having a drum, said drum having a liquid phase and a vapor phase above said liquid phase, wherein a heat exchange fluid circulates via a first conduit from said reactor to said drum and a second conduit from said drum to said reactor, and wherein a portion of said fluid is lost from said reactor system and makeup fluid is added to said reactor system, the improvement comprising adding said makeup fluid and said first conduit into the same phase of said drum; and also preferred embodiments selected from one or more of the following, which may be combined as would be recognized as appropriate by one of ordinary skill in the art in possession of the present disclosure: wherein said makeup fluid and said first conduit are added to said drum above the liquid phase; wherein said makeup fluid and said first conduit are added into said liquid phase of said drum; wherein said makeup fluid is added to said first conduit during at least a portion of said process; wherein said chemical reaction is selected from the polymerization of light olefins to make heavier olefins, the production of methanol, the production of mogas, and the production of cumene (and many other reactions, such as to make a liquid hydrocarbon suitable directly or as an intermediate for a combustion fluid or hydrocarbon fluid useful as, for instance, a solvent, carrier, etc.); wherein said reactor comprises a shell-and-tube reactor, particularly wherein said shell-and-tube reactor comprises tubes packed with a catalyst selected from sPA, zeolites, and mixtures thereof; wherein said system comprises plural reactors, each reactor having a drum fluidly connected thereto by said conduits, and each reactor comprising a shell-and-tube wherein each of said tubes in said system is packed with a catalyst which may be the same or different from any other tube in said system and wherein each reactor is independently allowed to approach isothermal conditions; wherein said heat exchange fluid in said first conduit comprises at least 5 wt % vapor; wherein makeup fluid is also added directly to said drum during at least a portion of said process; wherein makeup water is added exclusively to said first conduit during steady-state conditions. Also a continuous process for oligomerizing light olefins to heavier hydrocarbons, wherein a continuous liquid olefinic feedstream contacts an oligomerization catalyst under oligomerizing conditions in at least one tubular reactor fluidly connected with a drum whereby a heat exchanging fluid circulates between said tubular reactor and said drum, and wherein makeup fluid is added to account for lost heat exchanging fluid, the improvement comprising preheating said makeup fluid by contacting at least a portion of said makeup fluid with heat exchanging fluid exiting said tubular reactor before said heat exchanging fluid enters said drum; and also preferred embodiments selected from one or more of the following, which may be combined as would be recognized as appropriate by one of ordinary skill in the art in possession of the present disclosure: the process using a system comprising a plurality of tubular reactors, each reactor fluidly connect with a drum, and wherein at least two reactors are independently brought to a steady-state reaction condition by contacting at least a portion of said makeup fluid with heat exchanging fluid exiting said tubular reactor before said heat exchanging fluid enters said drum; wherein said steady-state reaction condition comprises substantially isothermal reaction conditions. Also an apparatus comprising a shell-and-tube reactor fluidly connected to a steam drum by at least two conduits, a first conduit for removal of fluid from said reactor to said steam drum and a second conduit for supply of fluid from said steam drum to said reactor, whereby a heat exchanging fluid can circulate between said reactor and said steam drum via said conduit, said apparatus further having at least one conduit whereby makeup heat exchanging fluid may be added, the improvement comprising having said at least one conduit enter said first conduit whereby makeup heat exchanging fluid may be added to the fluid in said first conduit; and a preferred embodiment wherein said apparatus is a retrofitted conventional waste heat boiler system further comprising a conduit whereby heat exchanging fluid may be added directly to said steam drum. Also a waste heat boiler system comprising at least one shell-and-tube heat exchanger fluidly connected with at least one drum and having a heat exchange fluid circulating via a first conduit from the shell side of said exchanger to said drum and a second conduit from said drum to the shell side of said heat exchanger, and wherein a portion of said fluid is lost from said waste heat boiler system and makeup fluid is added to said waste heat boiler system, the improvement comprising adding said makeup fluid to said first conduit; which may be further optionally described by one or more of the following: wherein said shell-and-tube heat exchanger comprises at least one tube having a catalyst disposed therein, said catalyst suitable for catalyzing an exothermic chemical reaction; wherein said catalyst comprises at least one catalyst selected from the group consisting of solid phosphoric acid (sPA), NiO on silica/alumina, $TiO_2$ dispersed on a monolayer of $SiO2$ on alumina support, and zeolites selected from ZSM-5, ZSM-22, ZSM-23, ZSM-35, ZSM-57, MCM-22, MCM-23, MCM-41, MCM-49, and MCM-56, which may or may not have metals deposited thereon or therein, and mixtures of these catalysts; and wherein said system further comprises plural shell-and-tube heat exchangers. Also in an oligomerization unit comprising: (a) at least one reactor and (b) a heat exchange circuit comprising a drum, the drum having therein a liquid phase and a vapor phase, the heat exchange circuit adapted to exchange heat with said reactor and comprising a first conduit from said reactor to said drum and a second conduit from drum to said reactor, a process comprising: (i) contacting an olefin feed and an oligomerization catalyst in the reactor thereby forming a reaction product; (ii) circulating a fluid through the heat exchange circuit from said reactor to said drum in said first conduit and from said drum to said reactor in said second conduit; and (iii) adding a substantially liquid-phase make-up fluid to said heat exchange circuit, wherein the make-up fluid and said first conduit enter the drum in the same phase; which may be further but optionally limited by at least one of the following conditions: wherein said make-up fluid and said fluid in said first conduit reach thermal equilibrium before entering said drum; wherein said make-up fluid and said fluid in said first conduit enter into the vapor phase of said drum; wherein said make-up fluid and said fluid in said first conduit enter into the vapor phase of said drum; wherein the catalyst is a solid phosphoric acid catalyst, a zeolite catalyst or a combination thereof; wherein the olefin feed comprises one or more C2-C10 α-olefins; wherein the olefin feed comprises propylene, n-butene, isobutene or any combination thereof; and wherein a recycle component is separated from said reaction product (the recycle component, in an embodiment, advantageously selected from the group consisting of a lower molecular weight oligomer, a saturate and an unreacted light olefin), which in an even more preferred embodiment is characterized by contacting the recycle product along with an olefin feed with an oligomerization catalyst to form said reaction product, yet still more preferably wherein the recycle component includes a lower molecular weight oligomer, and the reaction product comprises a distillate product; and also wherein said process further comprising removing a C6-C13 oligomer product from the reactor. It will be understood that the invention also pertains to processes wherein certain oligomer products may be further reacted, e.g., further reacting C6-C13 oligomer to form an aldehyde or alcohol and still further forming a plasticizer from the alcohols produced thereby, and yet still further forming an article of manufacture comprising a thermoplastic and the plasticizer.

All patents and patent applications and other documents cited herein are fully incorporated by reference to the extent such disclosure is not inconsistent with this invention and for all jurisdictions in which such incorporation is permitted.

What is claimed is:

1. In a reactor system comprising at least one reactor and a steam drum and having a heat exchange fluid circulating via a first conduit from said reactor to said steam drum and a second conduit from said steam drum to said reactor, and wherein a portion of said fluid is lost from said reactor system and makeup fluid is added to said reactor system via a makeup fluid conduit, said steam drum having contained therein a liquid phase and a vapor phase above said liquid phase, the improvement comprising adding said makeup fluid conduit and said first conduit into the same phase of said steam drum for controlling the reactor temperature.

2. The reactor system according to claim 1, wherein said makeup fluid conduit and said first conduit enter into the liquid phase contained within said steam drum.

3. The reactor system according to claim 1, wherein said makeup fluid conduit and said first conduit enter into the vapor phase contained within said steam drum.

4. The reactor system according to claim 1, the improvement further comprising one or more of the following: (i) adding said makeup fluid conduit into said first conduit, said first conduit entering said steam drum into said vapor phase; (ii) adding said first conduit into said makeup fluid conduit, said makeup fluid conduit entering said steam drum in said liquid phase; (iii) adding said first conduit and said makeup fluid conduit separately into said steam drum below the liquid level.

5. In a reactor system comprising at least one reactor and a steam drum and having a heat exchange fluid circulating via a first conduit from said reactor to said steam drum and a second conduit from said steam drum to said reactor, and wherein a portion of said fluid is lost from said reactor system and makeup fluid is added to said reactor system, the improvement comprising adding said makeup fluid to said first conduit for controlling the reactor temperature.

6. The reactor system of claim 5, wherein said reactor is a shell-and-tube polymerization reactor comprising at least one tube having a polymerization catalyst therein.

7. The reactor system of claim 6, wherein said catalyst is selected from the group consisting of solid phosphoric acid (SPA), zeolites, and mixtures thereof.

8. The reactor system of claim 5, wherein said drum is a steam drum having steam discharge outlet, an inlet to receive water/steam from said reactor, and an outlet comprising a conduit to said reactor.

9. The reactor system of claim 5, comprising at least two reactors, each reactor having a steam drum fluidly connected thereto.

* * * * *